(12) United States Patent
Liu et al.

(10) Patent No.: US 9,987,247 B2
(45) Date of Patent: Jun. 5, 2018

(54) DRUGS FOR TREATING DISEASES OF CERVICAL AND/OR LUMBAR VERTEBRAE

(71) Applicant: Li Liu, Foshan (CN)

(72) Inventors: Li Liu, Foshan (CN); Lifang Hu, Foshan (CN)

(73) Assignee: Li Liu, Foshan (CN)

( * ) Notice: Subject to any disclaimer, the term of this patent is extended or adjusted under 35 U.S.C. 154(b) by 0 days. days.

(21) Appl. No.: 15/039,635

(22) PCT Filed: Nov. 28, 2014

(86) PCT No.: PCT/CN2014/092506
§ 371 (c)(1),
(2) Date: Jun. 1, 2016

(87) PCT Pub. No.: WO2015/078413
PCT Pub. Date: Jun. 4, 2015

(65) Prior Publication Data
US 2017/0165221 A1    Jun. 15, 2017

(30) Foreign Application Priority Data
Nov. 28, 2013 (CN) .......................... 2013 1 0632900

(51) Int. Cl.
*A61K 31/343* (2006.01)
(52) U.S. Cl.
CPC ................................. *A61K 31/343* (2013.01)

(58) Field of Classification Search
CPC .................................................... A61K 31/343
See application file for complete search history.

(56) References Cited

FOREIGN PATENT DOCUMENTS

| | | |
|---|---|---|
| CN | 102429881 A | 5/2012 |
| CN | 102659727 A | 9/2012 |
| WO | 2006/058008 A1 | 6/2006 |

OTHER PUBLICATIONS

Weinstein et al. Spine (Phila PA 1976) Dec. 2008 1:33 (25).*
International Search Report for PCT/CN2014/092506, dated Mar. 3, 2015, 3 pages.
Kao, Ming-Chien, et al., "Thoracic Cord Compression Due to Gout: A Case Report and Literature Review," J Formos Med Assoc, vol. 99, No. 7, pp. 572-575, 2000.
Supplemental Search Report, Search Strategy, and Search Opinion for EP 14866401.4, 8 pages, dated Jun. 19, 2017.

* cited by examiner

*Primary Examiner* — Zohreh A Fay
(74) *Attorney, Agent, or Firm* — Banner & Witcoff, Ltd.

(57) ABSTRACT

The present invention relates to a benzbromarone or different pharmaceutically acceptable crystals thereof, or pharmaceutically acceptable solvates, salts, esters, ethers or clathrates thereof, or use of a pharmaceutical composition comprising any of the above in preparation of drugs, application thereof being for preparation of drugs for treating and preventing vertebrae cervicales diseases or lumbar disk herniation (LDH) in human.

2 Claims, No Drawings

DRUGS FOR TREATING DISEASES OF CERVICAL AND/OR LUMBAR VERTEBRAE

FIELD OF THE INVENTION

The invention relates to the field of medical technology, specifically intended to provide drugs for treating and preventing cervical spondylosis or lumbar disk herniation in human.

BACKGROUND OF THE INVENTION

The cervical spondylosis, also known as cervical syndrome, is a disorder based on degenerative pathological changes. In China, the incidence of cervical spondylosis is increasing. It was reported that the incidence of cervical disease nationwide is more than 20% with computer users, mobile phone users and office workers being at high risk. Besides, the onset of cervical spondylosis tends to occurs at younger ages, with the incidence among primary and secondary school students on a sharp rise. About 30% of patients at Orthopedics Department seek cervical spondylosis treatment.

The lumbar disk herniation (LDH), a kind of disorder in lumbar intervertebral discs named by American Academy of Orthopaedic Surgeons as intervertebral disk bulging, protruded intervertebral disc, extruded intervertebral disc, is a medical condition affecting the spine in which various parts (nucleus pulposus, fibrous ring and cartilage plate) of lumbar intervertibral disc take on degenerative pathological changes of different degrees and fibrous rings are ruptured under the effect of external factors, allowing the nucleus pulposus to bulge out through the rupture, which in turn stimulates or oppresses the surrounding tissues with resulting clinical manifestations of pain, numbness, soreness and other symptoms in waist and legs. It is a one of the common lumbar disorders in clinic, typically occurring in 10% to 15% of orthopaedic outpatients with low back pains and 25% to 40% of inpatients with waist and leg pains. This disease mostly occurs at the ages of 20 to 40 years old, and male patients outnumber female patients. It is shown in literatures that in US the incidence of LDH is 3.1% in male population and 1.3% in female population. Many literatures also reported the epidemiological profiles of LDH in China, and the literatures on Internet indicated an incidence of 15.2%. Many rigorous studies in the past disclosed the incidence in different circumstances. For example, in the Reference 1 [Lu Jun, etc. *Investigation on the Prevalence of Lumbar Disk Herniation in the Aircrew at Guangzhou Areas of China Southern Airlines*, Chinese Journal of Aerospace Medicine, 2008, (1) 62:132], 132 LDH patients was identified in the investigated 2495 people, resulting in an incidence of 5.3%; in the Reference 2 [Zhang Qishan, *Epidemiological Survey of Lumbar Disk Herniation in Flight personnel*, Chinese J. Convalescent Med, 2011 (9): 854-855;] the cumulative incidence of LDH in 757 active flight personnel was found to be 3.17%, which comprises 4.73% in fighters, 5.07% in trainers, 1.06% in bombers and 3.01% in transport aircrafts; in the Reference 3 [Wang Guo-ji, Wang Guo-jun, Peng Jian-min, etc, *Epidemiological Survey on the causing factors of Lumbar Disk Herniation*, Modern Preventive Medicine, 2009, 36 (13): 2401-2403;] four prefecture-level cities in Hunan Province was found to have a high incidence rate of 7.62% of LDH in various populations; in Reference 4 [Xie Zhaofeng etc. *Epidemiological Survey of Lumbar Disk Herniation without symptoms among soldiers in a troop*, J Prev. Med Chin PLA, 2002, Vol. 20 (6): 412-414;] the incidence of LDH without symptoms was investigated in a troop to support early prevention and treatment of LDH. This study randomly selected 219 new soldiers showing no symptoms in a troop for lumbar CT scan and found an incidence rate of 33.33% in these soldiers. The history of LDH is associated with gender, age, profession characteristics, trauma history and cold history. Its early intervention is predominated by conservative treatment methods such as bed rest, traction, physiotherapy and drugs. However, currently there is a deficiency in specific drugs and in drug diversity.

The cervical disc herniation (CDH) is also extensively discussed in literatures with an incidence rate being second only to that of lumbar disk herniation. It is caused by the degenerative pathological changes of fibrous ring, nucleus pulposus of cervical intervertebral disc and cartilage plate, in particular nucleus pulposus of cervical vertebrae, when fibrous rings are ruptured under the effect of external factors, allowing the nucleus pulposus tissues to bulge out through the rupture or to extrude into spinal canal, which in turn oppresses the surrounding tissues such as spine nerve roots or spinal cord with resulting clinical manifestations of dizziness, headache, chest distress, palpitation, cervical movement limitation, soreness, pains in shoulder back, numbness and pains in upper limbs, gait disturbance, weakness of limbs and other symptoms and signs, and even life-threatening high paraplegia in the worst case. The incidence of CDH ranks only second to that of LDH among intervertebral disc disorders, accounting for about 40%. It mostly occurs in populations aged 40 years old above with a male-to-female prevalence ratio of 1.4:1 (Reference: Wang wen, *Development in the Diagnosis and Treatment of cervical disc herniation*, 2012, 18 (3):129).

The cervical spondylosis or LDH, if treated improperly or not timely, may lead to cervical vertebral or lumbar malformation, and with the development of the illness, can result in the deterioration of intervertebral disc herniation, increased nucleus pulposus bulging, deflection in spinal formation, humpback and other complications. In addition, this case will be subject to aggravation of pain in neck or waist, which is more intense during the night, and eventually lead to functional disorders in the flexion and extension of neck or waist with secondary severe symptoms including numbness of limbs, limitation of weight bearing and mobility, which directly influence the work, study and life of patients.

Currently, there are a variety of methods available for treating cervical spondylosis or LDH as follows, for example:

(1) Non-surgical drug treatment: take analgesic drugs and apply analgesic plasters to alleviate local pain;

(2) Partial closure therapy: the partial closure treatment of cervical or lumbar vertebrae consists of acupoint block and regional block, which requires superior techniques;

(3) Open surgery: a) In case of forward disc herniation in cervical segments, this operation may cause damage to the large cervical vascular and nerve, or in case of forward disc herniation in thoracic segments where the surgery must take thorax approach, this operation may lead to a series of sequelae such as mediastinum viscera injury and postoperative hemopneumothorax, pleural adhesion, prolonged chest pain, etc.; b) The surgery for lumbar disk herniation is to excise the pathological nucleus pulposus directly to relief radicular pain. Due to the limitation of particular physical position of lumbar spine, such surgery will cause damage to the normal lumbar physiological structure, which often results in postoperative lumbar spinal instability, postoperative scar tissue adhesions, and accidental nerve injury, and other adverse reactions. Therefore, most patients are afraid of surgery, and the question how to avoid these adverse reactions caused by surgery constantly plagues the medical professions. In general, surgical treatment can be both risky and costly;

(4) Traction therapy which is mainly intended to stretch the ligaments around the cervical and lumbar to ease the pain for a short time by using a special traction device. Nevertheless, the therapy requires special equipment and professional operators, such as SDS non-surgical spinal decompression system, along with the high cost;

(5) Plasmin injection for treating LDH and CDH which has the risk of causing complications. For example, if the drug is incorrectly injected into intervertebral foramen, spinal nerve roots will be injured and in turn lead to numbness of limbs or sensory disability; if the drug is incorrectly injected into spinal canal, severe complications such as acroparalysis may be caused;

(6) Physiotherapy: (6.1) short-wave or ultrashort wave therapy, one time per day, 20-40 mins per time, 15-20 times as one course of treatment; (6.2) diadynamic therapy, one or two times per day, 15-20 times as one course of treatment; (6.3) ultrastimulation electrotherapy. All these physical therapies have the disadvantages of slow recovery, long course, poor effect and dependence on treatment instrument;

(7) Ozone therapy: ozone of high concentration has the effect of astringency and vaporization which is used to treat CDH or LDH. In theory, the injection of ozone can astringe and vaporize lumbar nucleus pulposus. However the entry of ozone into spinal canal will lead to adverse reactions and complications, and the success rate of this therapy is not high;

(8) Microendoscopic discectomy of minimally invasive surgery: in addition to surgical risks and complications, such surgery has one main disadvantage of narrowed operative visual field, making it difficult to clearly and thoroughly excise the pathological nucleus pulposus, thus increasing the risk of operation failure;

(9) Percutaneous atherectomy, having the risk of operation failure, etc.;

(10) Acupuncture treatment, having the disadvantage of high dependency on the personnel medical capacity of the doctor, inconveniency, etc.

Therefore, new treatment approaches or drugs are being searched for constantly to treat or prevent cervical spondylosis, LDH or the like.

DETAILED DESCRIPTION OF THE INVENTION

At present, the benzbromarone or benzene-bromine-coumarin (molecular formula: $C_{17}H_{12}Br_2O_3$ and CAS: 3562-84-3) is universally accepted and known to be used to treat the chronic gout and hyperuricemia alone or in combination with other drugs (Shang Guang, Li Dakui, *Modern Clinical Pharmacology, Chemical industry press*, Beijing, 2003, p 274). So far there has not any public document or report reporting that the benzbromarone or benzene-bromine-coumarin can be used to treat the vertebrae cervicales diseases (including CDH) or LDH, which means this drug is not in the publicly known state in treating the vertebrae cervicales diseases or LDH.

The present invention aims at providing a kind of drug to treat the vertebrae cervicales diseases or LDH—the benzbromarone or benzene-bromine-coumarin or its derivate or clathrate. The typical administration manner of this drug is oral administration without injection, which can reduce the inconvenience of looking for injection point and the risk brought by intravenous therapy, ease the burden of the injection treatment for nurses, reduce the dependency on and inconvenience of instrumental therapy and facilitate the treatment for patients. It provides a new kind of effective, safe and reliable drug in the clinic treatment of the cervical spondylosis or LDH.

The present invention provides the patients with a convenient method with high safety, reliable effect, low cost and ready administration to treat the cervical spondylosis or LDH without surgery. For the patients having to stay in bed, they can quickly restore their abilities to walk or work.

Furthermore, the present invention relates to provides the use of a benzbromarone or benzene-bromine-coumarin or different pharmaceutically acceptable crystals thereof, or pharmaceutically acceptable solvates, salts, esters or clathrates thereof, or a pharmaceutical composition comprising any of the above in preparation of a medicament for treating or preventing vertebrae cervicales diseases or LDH in human; or, the use or application of the above in preparation of a medicament for treating or preventing vertebrae cervicales diseases or LDH or the pharmaceutical composition containing the drug of the present invention. This therapeutic use includes but not limited to the use of preparing the therapeutic drugs, which are used in auxiliary or combined therapeutic schedule.

When the benzbromarone is used to treat or prevent diseases of vertebrae cervicales and/or vertebrae lumbales, the different pharmaceutically acceptable crystals thereof, or pharmaceutically acceptable solvates, salts, esters, ethers, clathrates, lipidosomes or micro-emulsions thereof shall have the same use.

In another aspect, the present invention provides a kind of drug for treating or preventing vertebrae cervicales diseases or LDH, or the pharmaceutical composition containing the drug. The pharmaceutical composition includes any effective dose of benzbromarone, different crystals thereof, or pharmaceutically acceptable solvates, salts, esters, ethers or clathrates thereof, and one or more pharmaceutically acceptable excipient, diluent or carrier.

The pharmaceutically acceptable clathrate of the present invention includes but not limited to the clathrate of the cyclodextrin and cyclodextrin derivatives. It is not limited to include β-cyclodextrin, α-cyclodextrin, γ-cyclodextrin and the clathrate thereof. Further, benzbromarone of the present invention can be prepared into such liquid formulations as oral solution or suspension solution etc., external use patch or such solid formulations as tablets, capsules, granules and guttate pills etc., which are all used for preventing and treating vertebrae cervicales diseases or LDH. When used for preparing the formulations with corresponding therapeutic use, the formulation types also include dispersible tablets, mouth-dissolving tablets, lipidosomes, micro-emulsions or injections etc.

When used for preparing the pharmaceutically acceptable composition, the drug of the present invention can contain the pharmaceutically acceptable excipients; when used for preparing tablets (including buccal tablets, dispersible tablets, fast disintegrating tablets and vaginal tablets), capsules (including vaginal capsules) and granules, the formulations can contain pharmaceutically acceptable fillers, such as starch, modified starch, lactose, microcrystalline cellulose, cyclodextrin, sorbitol, mannitol, calcium phosphate, amino acids, etc.; pharmaceutically acceptable disintegrants, such as starch, modified starch, microcrystalline cellulose, cross-linked carboxymethyl cellulose, sodium carboxymethyl starch, crosslinked polyvinylpyrrolidone, low substituted hydroxypropyl cellulose, surface active agents (sodium lauryl sulfate, etc.); pharmaceutically acceptable wetting agent and binder, such as gelatinised starch, methyl cellulose, sodium carboxymethyl cellulose, ethyl cellulose, polyvinylpyrrolidone, alginic acid and salts thereof etc; pharmaceutically acceptable lubricant and glidant, such as stearic acid, magnesium stearate, polyethylene glycol 4000 to 8000, talc, fine powder silica gel, magnesium lauryl sulfate, etc.; and pharmaceutically acceptable sweeteners and flavors, such as aspartame, sodium cyclamate, sodium saccharin, sucralose and edible essence etc.

The process that any pharmaceutically acceptable solvates, salts, esters, ethers or clathrates of benzbromarone is absorbed or degraded in the body or degraded metabolically by the enzyme in the body into the active ingredient benzbromarone to play a role of prevention or treatment is not contrary to the spirit of the present invention and is within the scope of the present invention. Under such circumstances, the blood concentration of benzbromarone is equivalent to performing the treating effect within the effective dose of benzbromarone through gastrointestinal administration. The ester synthesis of benzbromarone can utilize its phenolic hydroxyl group and such pharmaceutically acceptable acid as formic acid, acetic acid, propionic acid, butyric acid and valeric acid etc; the ether synthesis of benzbromarone can utilize its phenolic hydroxyl group and methyl alcohol, ethyl alcohol, propyl alcohol or derivates thereof etc.

Orally administered usage and dosage of the benzbromarone or benzene-bromine-coumarin: under normal circumstances, the dosage of administration or its range is determined by the patients' weights. It can be 6-200 mg/time; or 0.1-3.5 mg/kg, preferably 0.4-2.0 mg/kg; for adults aged over 18 and weighing about 45-80 kg, gastrointestinal administration, usually oral administration: 12.5-100 mg/time and one to two times a day; for children, more than a half dose shall be reduced. For the gastrointestinal administration of adults, the relatively preferred daily dosage is 25-100 mg/time, the more preferred daily dosage is 50-100 mg/time. When the drug is difficult to be administrated orally, the buccal or sublingual administration etc. can be adopted.

The present invention is different from the traditional Chinese medicine with complex ingredients. For the traditional Chinese medicine, it is difficult to control all components of one or more traditional Chinese medicinal materials in a complex system. However, the present invention is of a single chemical component. Therefore, it is easy to control the quality of preparation to ensure the accuracy and safety of clinical administration etc.

SPECIFIC MODE OF EXECUTION

All the numerical values used in the specification and claims, apart from those in the examples and otherwise indicated, should be understood to be modified with the term 'about' in all the examples. Therefore, unless there are contrary instructions, the numerical parameters given in the present specification are approximations, which may vary with the desired properties sought in the content disclosed in the present invention. At least, and not intended to limit the application of Doctrine of Equivalents of the claimed scope, each numerical parameter should be explained by considering the number of significant digits and conventional rounding method.

Although the numerical ranges and parameters in broad scope defined in the present invention are approximations, the numerical values provided in the specific examples are reported as precisely as possible. Any numerical value substantially contains some errors necessarily generated from the standard deviation found in their respective test.

It should be noted, unless otherwise definitely indicated in the context, the singular forms "a", "an" and "the" used in the specification and claims include the plural forms of the object; therefore, for example, a composition comprising "a compound" includes a mixture of two or more compounds. In addition, it should be noted that the term "or" normally includes "and/or", unless otherwise explicitly stated in the context.

Pharmaceutical composition: The term "pharmaceutical composition" used in the context means a composition of drug. The said pharmaceutical composition may contain at least one pharmaceutically acceptable carrier.

As used herein, "pharmaceutically acceptable excipient" means a pharmaceutically acceptable carrier or solvent media suitable for the administration of compounds provided in the present invention, including any carrier suitable for particular administration manner known in the art, e.g., solutions or suspensions for parenteral, intradermal, subcutaneous, or topical application can include a sterile diluent (e.g., water for injection, saline solution, non-volatile oil, etc.); synthetic fat solvent media (e.g., polyethylene glycols, glycerine, propylene glycol, etc.); antibacterial agents (e.g., benzyl alcohol, methylparaben, ethylparaben, etc.); antioxidants (e.g., ascorbic acid, sodium bisulfite, etc.); chelating agent (i.e., EDTA, etc.); buffer agent (phosphate, citrate, etc.); and/or their mixtures.

As non-limiting examples, the benzbromarone or benzene-bromine-coumarin can be optionally mixed with one or more pharmaceutically acceptable excipients, and can be orally administered in following forms (but not limited to oral administration or gastrointestinal administration): tablets, capsules, dispersible powders, granules, or suspensions containing, e.g. about 0.05% to 5% suspending agent; or parenterally administered in forms of sterile solutions or suspensions, the latter of which contain 0.05% to 5% suspending agent in isotonic medium. These pharmaceutical preparations may contain, e.g. from about 25% to about 90% of active ingredient and a carrier, more typically containing 5% to 60% (by weight) of active ingredient.

The evaluation criteria on the treatment effect of the present invention on CDH and LDH:

(1) Cure: complaining of pain, body pain and pain behavior (moaning, gait, loss of position posture) disappeared, and recovery of the ability to work; (2) Remarkable improvement effects: obviously reduced complaining of pain and body pain, no obvious pain behavior disappears, and recovery of the ability to work; (3) Improvement effective: reduced complaining of pain, body pain and pain behavior; (4) Unhealed: the same as the situation before treatment.

The clinical effect criteria of the drug of the present application for treating cervical spondylosis can also be evaluated 2 weeks after treatment. (1) Cure: pains in neck, shoulders, and arms disappeared, and no numbness in upper limbs; (2) Remarkable improvement effects: pains in neck, shoulders, and arms, and upper limb numbness significantly reduced; (3) Effectiveness: pains in neck, shoulders, and arms, and upper limb numbness pain relieved, but there is still a sense of neck aching and feebleness; (4) Ineffectiveness: symptoms and signs don't improve obviously and even get worse.

The present invention shows remarkable treatment effect after being used in corresponding treatment.

In order to further illustrate the present invention, the following preferred embodiments of the present invention are described with examples (including the description of characteristic condition, characteristic symptom or characteristic data which are beneficial to illustrate the effect of the present invention), but it should be understood that these descriptions are only for further illustration of the features and advantages of the present invention, not limitation of the scope of the present invention.

The effects of the present invention are described below with the specific examples, but the protection scope of the present invention is not limited by the examples below.

EXAMPLES

Example 1. Preparation of Benzbromarone Tablets, and Preparation of Pharmaceutical Composition (Benzbromarone 12.5 mg/Tablet)

Formulation:
Benzbromarone: 125 g
Microcrystalline cellulose: 750 g
Sodium carboxymethyl starch: 50 g
Polyvinylpyrrolidone 5%: appropriate amount
Magnesium stearate: 4 g
Benzbromarone, microcrystalline cellulose and sodium carboxymethyl starch were screened through 100 mesh sieve, and prepared into soft material with an appropriate amount of 5% polyvinylpyrrolidone (prepared with 95% alcohol/water), granulated through 18-24 mesh sieve, dried, passed through 14-20 mesh sieve, added magnesium stearate which is pre-screened through 100 mesh sieve, mixed and compacted into tablets.

Example 2. Preparation of Benzbromarone Capsules, and Preparation of Pharmaceutical Composition (Benzbromarone 12.5 mg/Granulate)

Formulation:
Benzbromarone: 125 g
Microcrystalline cellulose: 600 g
Lactose: 275 g
Hydroxypropyl methyl cellulose 5%: appropriate amount
Magnesium stearate: 3 g
Benzbromarone, microcrystalline cellulose and lactose were screened through 100 mesh sieve, and prepared into soft material with an appropriate amount of 5% hydroxypropyl methyl cellulose (prepared with 90% alcohol/water), granulated through 24-30 mesh sieve, dried, passed through 24-30 mesh sieve, added magnesium stearate which is pre-screened through 100 mesh sieve, mixed and encapsulated.

Example 3. Preparation of Benzbromarone Tablets, and Preparation of Pharmaceutical Composition (Benzbromarone 25 mg/Tablet)

Formulation:
Benzbromarone: 250 g
Microcrystalline cellulose: 1200 g
Sodium carboxymethyl starch: 50 g
Polyvinylpyrrolidone 5%: appropriate amount
Magnesium stearate: 5 g
Benzbromarone, microcrystalline cellulose and sodium carboxymethyl starch were screened through 100 mesh sieve, and prepared into soft material with an appropriate amount of 5% polyvinylpyrrolidone (prepared with 95% alcohol/water), granulated through 18-24 mesh sieve, dried for about two hours at 52° C., passed through 14-20 mesh sieve, added magnesium stearate which is pre-screened through 100 mesh sieve, mixed and compacted into tablets.

Example 4. Preparation of Benzbromarone Capsules, and Preparation of Pharmaceutical Composition (Benzbromarone 25 mg/Granulate)

Formulation:
Benzbromarone: 250 g
Microcrystalline cellulose: 700 g
Sodium carboxymethyl starch: 30 g
PVP-K30 5%: appropriate amount
Magnesium stearate: 5 g
Benzbromarone, microcrystalline cellulose and sodium carboxymethyl starch were screened through 100 mesh sieve, and prepared into soft material with an appropriate amount of 5% PVP-K30 (prepared with 95% alcohol/water), granulated through 18-24 mesh sieve, dried, passed through 14-20 mesh sieve, added magnesium stearate which is pre-screened through 100 mesh sieve, mixed and encapsulated.

Example 5. Preparation of Benzbromarone Capsules, and Preparation of Pharmaceutical Composition (Benzbromarone 100 mg/Granulate)

Formulation:
Benzbromarone: 200 g
Lactose: 30 g
Microcrystalline cellulose: 50 g
Sodium carboxymethyl starch: 20 g
PVP-K30 5%: appropriate amount
Fine powder silica gel: 5 g
Benzbromarone, lactose, microcrystalline cellulose and sodium carboxymethyl starch were screened through 100 mesh sieve, and prepared into soft material with an appropriate amount of 5% PVP-K30 (prepared with 95% alcohol/water), granulated through 18-24 mesh sieve, dried for about three hours at 50° C. or below, passed through 14-20 mesh sieve, added fine powder silica gel which is pre-screened through 100 mesh sieve, mixed and encapsulated.

Example 6. Preparation of Benzbromarone Tablets, and Preparation of Pharmaceutical Composition (Benzbromarone 100 mg/Tablet)

Formulation:
Benzbromarone: 100 g
Microcrystalline cellulose: 80 g
Lactose: 20 g
Crosslinked polyvinylpyrrolidone: 10 g
Low substituted hydroxypropyl methyl cellulose: 10 g
Sodium carboxymethyl starch: 20 g
PVP-K30 5%: appropriate amount
Fine powder silica gel: 5 g
Benzbromarone, lactose, microcrystalline cellulose, crosslinked polyvinylpyrrolidone, low substituted hydroxypropyl methyl cellulose and sodium carboxymethyl starch were screened through 100 mesh sieve, and prepared into soft material with an appropriate amount of 5% PVP-K30 (prepared with 95% alcohol/water), granulated through 18-24 mesh sieve, dried for about two hours at 55° C., passed through 14-20 mesh sieve, added fine powder silica gel which is pre-screened through 100 mesh sieve, mixed and compacted into tablets.

Example 7. Preparation of Benzbromarone Capsules, and Preparation of Pharmaceutical Composition (Benzbromarone 50 mg/Granulate)

Formulation:
Benzbromarone: 50 g
Lactose: 30 g
Microcrystalline cellulose: 20 g
Sodium carboxymethyl starch: 8 g
PVP-K30 5%: appropriate amount
Fine powder silica gel: 2 g
Benzbromarone, lactose, microcrystalline cellulose and sodium carboxymethyl starch were screened through 100 mesh sieve, and prepared into soft material with an appropriate amount of 5% PVP-K30 (prepared with 95% alcohol/water), granulated through 18-24 mesh sieve, dried for about two hours at 55° C., passed through 14-20 mesh sieve, added fine powder silica gel which is pre-screened through 100 mesh sieve, mixed and encapsulated.

Example 8. Preparation of Benzbromarone Tablets, and Preparation of Pharmaceutical Composition (Benzbromarone 50 mg/Tablet)

Formulation:
Benzbromarone: 50 g
Lactose: 20 g
Microcrystalline cellulose: 30 g
Sodium carboxymethyl starch: 10 g
Sodium lauryl sulfate: 1 g
PVP-K30 5%: appropriate amount
Fine powder silica gel: 3 g
Benzbromarone, lactose, microcrystalline cellulose, sodium lauryl sulfate and sodium carboxymethyl starch were screened through 100 mesh sieve, and prepared into soft material with an appropriate amount of 5% PVP-K30 (prepared with 95% alcohol/water), granulated through 18-24 mesh sieve, dried, passed through 14-20 mesh sieve, added fine powder silica gel which is pre-screened through 100 mesh sieve, mixed and compacted into tablets.

Example 9. Preparation of Benzbromarone Granules (Benzbromarone 25 mg/Package)

Formulation:
Benzbromarone: 25 g
Mannitol: 20 g
Lactose: 150 g
Sodium cyclamate: 2 g
Solid edible essence: 1 g
Xanthan gum: 2 g
8% solution of PVP-K30 in alcohol/water: appropriate amount
Benzbromarone, mannitol, lactose, sodium cyclamate and edible essence were screened through 100 mesh sieve, and prepared into soft material with an appropriate amount of 8% solution of PVP-K30 in alcohol/water, granulated through 18-24 mesh sieve, dried for about two hours at 60° C. or below, added xanthan gum which is pre-screened through 100 mesh sieve, passed through 14-20 mesh sieve, mixed, added xanthan gum which is pre-screened through 100 mesh sieve, and packaged.

Example 10

Patient A, male, 48 years old, about 75 kg, had a history of lumbar disc herniation, caused by coldness and fatigue, with the symptom of feeling that the upper body separates from lower body from at the waist, waist pain accompanied by the lower limb radiation pain, Straight leg raising test (+), difficulty in walking, and needing bed rest. The patient took benzbromarone once a day, 100 mg on the first day, and each 50 mg on and after two days. During the therapy, the patient rested in a hard board bed without additional treatments. The painful symptoms lessened after one day, and alleviated obviously after two days and the patient was able to walk. After a continuous administration for five days, Straight leg raising test (−), the patient could walk properly with the pain basically disappeared. By caring not to catch cold or get tired, the symptoms haven't occurred within the next six months, and the patient walked properly.

Example 11

Patient B, male, adult, 29 years old, about 60 kg, with lumbar disc herniation caused by sport incident, waist pain accompanied by the bottom and lower limb radiation pain, and aggravated when coughing or sneezing, Straight leg raising test (+). The patient took benzbromarone once a day, 50 mg each time, sitting or lying down to rest, and enhanced by massaging waist once per day, within two days after administration. The painful symptoms alleviated obviously after two days. After a continuous administration for seven days, Straight leg raising test (−), the waist pain basically disappeared, no perceptible pain during severe coughing, the patient being able to walk and work. During the treatment no other drugs suitable for this disease were used. After the symptoms disappeared, the patient exercised properly and paid attention to prevent the waist from coldness and exertion, no recurrence occurred within the next three months and the patient walked normally.

Example 12

Patient C, male, adult, 36 years old, with a history of lumbar disc herniation. Fatigue led to recurrence of lumbar disc hernia. The patient had a waist pain accompanied by the lower limbs radiation pain, and walk difficultly. Straight leg raising test was positive. The patient took benzbromarone once a day, each 12.5 mg, sitting or lying down to rest, and having waist massaged once a day within two days after the administration. Six days later, the pain was significantly lessened. After a continuous administration for six days, Straight leg raising test was negative, the patient walked properly and was able to work, the symptoms of pain disappeared. There was no recurrence occurred within the next two months, and the patient walked normally.

Example 13

Patient D, female, adult, with a history of lumbar intervertebral disc protrusion (L4/5), caused by exertion during work. The patient has the symptoms of waist pain, accompanied by the lower limb radiation pain. Straight leg raising test was positive. The patient took benzbromarone once a day, each 50 mg, sitting or lying down to rest, without any other treatments. Three days later, the pain was significantly lessened. After a continuous administration for six days, Straight leg raising test was negative, and the patient walked properly and was able to work without pain. There was no recurrence occurred within the next three months.

Example 14

Patient E, female, adult, with a history of cervical intervertebral disc herniation, fatigue, dizziness, pain in head and neck, discomfort in neck, upper limbs numbness, the Fenz, Eaten and Spurling signs were positive. The patient took benzbromarone once a day, each about 50 mg, six days in a row, without other treatment. Six days later, her symptoms in pain, upper limbs numbness and dizziness relieved.

Example 15

Patient F, male, adult, had a history of lumbar disc herniation. Fatigue led to recurrence of lumbar disc hernia. The patient had waist pain accompanied by lower limbs radiation pain, and difficulty walking. Straight leg raising test was positive. The patient took benzbromarone once a day, each about 25 mg, sitting or lying down to rest, and having waist massaged once a day within the first three days after administration. Three days later, the pain was significantly lessened and the patient was able to walk. After a continuous administration for six days, the patient walked properly and no recurrence occurred within the next two months.

Example 16

Patients G, female, had a history of cervical disease, onsets after fatigue, with the symptoms of feeling dizziness, neck stiffness, discomfort and pain. the Fenz and Spurling signs were positive. The patient took benzbromarone once a day, each about 25 mg, for eight days, having neck massaged once a day in the first three days after administration, constantly paying attention to the neck posture both during work and at rest, without any other treatment. Eight days later, the pain and dizziness symptoms disappeared and the Fenz signs was negative.

Example 17

Patients H, male, adult, about 62 kg, had protrusion of intervertebral disc (protrusion of L3/4 intervertebral disc) due to inadvertent movement. The patient felt waist pain, which aggravated while coughing and sneezing. The pain radiated to the buttocks and lower limbs. Physical examination found that the Straight leg raising test was positive. The patient took benzbromarone once a day, each 100 mg, for six days; and sodium bicarbonate tablets 0.5 g/time, three times a day; drank about 2000 ml water daily, sitting or lying down to rest, without any other treatment. Two days later, the pain was significantly reduced. After a continuous administration for six days, the Straight leg raising test was negative, his waist pain basically disappeared, no pain was felt when coughing, the patient could walk normally, and was able to work. After the symptoms disappeared, the patient exercised properly and paid attention to prevent waist from coldness and exertion. No recurrence occurred within the next three months and the patient walked normally.

Example 18

Patient I, female, 40 years old and about 55 kg, had a history of cervical disc herniation. After fatigue, the patient felt dizziness, head and neck pain, neck discomfort, and upper extremity numbness. The flexion neck rotation test, brachial plexus plexus traction test positive, and foraminal compression test were positive. The patient took benzbromarone capsules twice a day, each 50 mg, and took sodium bicarbonate tablets 0.5 g/time, three times a day, drank about 2000 ml water daily, and no other means of treatment was applied. After three days, the dizziness symptoms reduced significantly. She paid attention to the rationality of neck posture while working and at rest during the treatment, and didn't receive any other means of treatment. After a continuous administration for eight days, the pain and dizziness symptoms disappeared, flexion neck rotation test was negative, and no recurrence occurred within the next one months.

Example 19

Patient L, male, 44 years old, about 68 kg, with a the history of a lumbar intervertebral disc protrusion (L4/5), caused by overworking, who has the syndrome of waist pain, accompanied by the lower limb radiation pain, walking difficulties. Bragard test was positive. The patient orally took benzbromarone, once a day, every time 100 mg; and sodium bicarbonate tablets 1 g/time, three times a day, with each time interval being about 12 hours; and drank water about 2500 ml/day; with sitting or lying down for a rest. Three days later, pain symptoms obviously relieved. After taking medicine for seven days, the Bragard test were negative, the pain basically disappeared, normal walking, work ability recovery. During the following two months, no relapse has occurred, and the patient walked normally.

INDUSTRIAL APPLICABILITY

The present invention is detailed with specific modes of execution and examples hereinabove, but it should be understood that the details do not limit the scope of the present invention. The relevant technicians can obviously, without deviation from the spirit and scope of protection of the present invention, modify, improve, replace and combine the technical solutions and its modes of execution of the present invention to realize the present invention technology. All these shall fall into the scope of protection of the present invention. It should be especially noted that it can be understood that the variations of many details are possible and all similar replacement and changes are obvious to the technicians in the art. All the variations are regarded as being included in the spirit, scope and content of the present invention. The present invention is not limited to the above examples or embodiments.

The invention claimed is:

1. A method for treating lumbar disk herniation, comprising administering to a patient in need thereof a benzbromarone or a pharmaceutically acceptable crystal, salt, ester, or ether thereof, or a pharmaceutical composition comprising a benzbromarone or a pharmaceutically acceptable crystal, salt, ester, or ether thereof, wherein a dosage of 0.1 to 3.5 mg/kg of benzbromarone is administered.

2. The method of claim 1, wherein the pharmaceutical composition is administered, wherein the pharmaceutical composition contains at least one pharmaceutically acceptable adjuvant which is a pharmaceutically acceptable excipient, diluent or carrier.

\* \* \* \* \*